US009572680B2

(12) United States Patent
Theofilos et al.

(10) Patent No.: US 9,572,680 B2
(45) Date of Patent: Feb. 21, 2017

(54) SPINAL IMPLANTS, SPINAL IMPLANT KITS, AND SURGICAL METHODS

(71) Applicant: K2M, Inc., Leesburg, VA (US)

(72) Inventors: Charles Theofilos, Palm Beach Gardens, FL (US); Scott Jones, Mcmurray, PA (US); Jennifer Moore, Summit Point, WV (US)

(73) Assignee: K2M, Inc., Leesburg, VA (US)

( * ) Notice: Subject to any disclaimer, the term of this patent is extended or adjusted under 35 U.S.C. 154(b) by 318 days.

(21) Appl. No.: 13/750,496

(22) Filed: Jan. 25, 2013

(65) Prior Publication Data

US 2014/0214166 A1    Jul. 31, 2014

(51) Int. Cl.
*A61F 2/44* (2006.01)
*A61F 2/46* (2006.01)
*A61F 2/30* (2006.01)

(52) U.S. Cl.
CPC ............ *A61F 2/4455* (2013.01); *A61F 2/4611* (2013.01); *A61F 2002/3082* (2013.01); *A61F 2002/30578* (2013.01); *A61F 2002/30604* (2013.01); *A61F 2002/30787* (2013.01); *A61F 2002/30904* (2013.01); *A61F 2002/4627* (2013.01)

(58) Field of Classification Search
CPC .......... A61F 2/442; A61F 2/44; A61F 2/4455; A61F 2/4611; A61F 2/446; A61F 2/4465; A61F 2/447
USPC ........................................... 623/17.11, 17.16
See application file for complete search history.

(56) References Cited

U.S. PATENT DOCUMENTS

| 5,397,364 A | 3/1995 | Kozak et al. |
| 5,755,796 A | 5/1998 | Ibo et al. |
| 6,066,175 A | 5/2000 | Henderson et al. |
| 6,106,557 A | 8/2000 | Robioneck et al. |
| 6,113,638 A | 9/2000 | Williams et al. |

(Continued)

FOREIGN PATENT DOCUMENTS

| WO | 02-03885 A2 | 1/2002 |
| WO | 2012/148500 A2 | 11/2012 |

OTHER PUBLICATIONS

International Search Report from corresponding International Application No. PCT/US2013/023164 dated Oct. 18, 2013.

*Primary Examiner* — Kevin T Truong
*Assistant Examiner* — Si Ming Ku
(74) *Attorney, Agent, or Firm* — Carter, DeLuca, Farrell & Schmidt, LLP (57) ABSTRACT

A spinal implant includes a body, plate, and bone screws. The body includes a first wall having second and third walls joined thereto to define legs. In an embodiment, the body and plate are of unitary construction. In alternative embodiments, the body is formed from a first material and is configured for positioning between vertebral bodies. In other embodiments, the body is separate from the plate. The plate has a main portion and a flange. The main portion has a first screw hole oriented towards the first vertebral body at an oblique angle relative to the horizontal axis of the body. The flange has a second screw hole oriented towards the second vertebral body and substantially parallel to the horizontal axis. The flange is coupled to the main portion and extends past the main portion. Each bone screw is insertable through a screw hole of the plate for attachment to bone. A kit including a body, bone screws, and a plurality of different plates is also provided.

19 Claims, 6 Drawing Sheets

(56) References Cited

U.S. PATENT DOCUMENTS

| | | |
|---|---|---|
| 6,228,118 B1 | 5/2001 | Gordon |
| 6,231,610 B1 | 5/2001 | Geisler |
| 6,235,059 B1 | 5/2001 | Benezech et al. |
| 6,342,055 B1 | 1/2002 | Eisermann et al. |
| 6,342,074 B1 | 1/2002 | Simpson |
| 6,423,095 B1 | 7/2002 | Van Hoeck et al. |
| 6,432,106 B1 | 8/2002 | Fraser |
| 6,458,159 B1 | 10/2002 | Thalgott |
| 6,461,359 B1 | 10/2002 | Tribus et al. |
| 6,471,724 B2 | 10/2002 | Zdeblick et al. |
| 6,485,517 B1 | 11/2002 | Michelson |
| 6,558,387 B2 | 5/2003 | Errico et al. |
| 6,558,423 B1 | 5/2003 | Michelson |
| 6,629,998 B1 | 10/2003 | Lin |
| 6,730,127 B2 | 5/2004 | Michelson |
| 6,805,714 B2 | 10/2004 | Sutcliffe |
| 6,972,019 B2 | 12/2005 | Michelson |
| 7,033,394 B2 | 4/2006 | Michelson |
| 7,112,222 B2 | 9/2006 | Fraser et al. |
| 7,163,561 B2 | 1/2007 | Michelson |
| 7,172,627 B2 | 2/2007 | Fiere et al. |
| 7,232,463 B2 | 6/2007 | Falahee |
| 7,232,464 B2 | 6/2007 | Mathieu et al. |
| 7,815,681 B2 | 10/2010 | Ferguson |
| 7,846,207 B2 | 12/2010 | Lechmann et al. |
| 7,850,731 B2 | 12/2010 | Brittan et al. |
| 7,887,595 B1 | 2/2011 | Pimenta |
| 7,972,363 B2 | 7/2011 | Moskowitz et al. |
| 7,985,255 B2 | 7/2011 | Bray et al. |
| 8,137,405 B2 | 3/2012 | Kostuik et al. |
| 2005/0177245 A1 | 8/2005 | Leatherbury et al. |
| 2006/0200134 A1* | 9/2006 | Freid ............... A61B 17/1728 606/71 |
| 2007/0250167 A1* | 10/2007 | Bray ................. A61F 2/4465 623/17.11 |
| 2008/0249569 A1 | 10/2008 | Waugh et al. |
| 2008/0249575 A1* | 10/2008 | Waugh ................ A61F 2/447 606/305 |
| 2008/0249625 A1 | 10/2008 | Waugh et al. |
| 2008/0294262 A1 | 11/2008 | Levieux |
| 2008/0300634 A1 | 12/2008 | Gray |
| 2008/0306596 A1 | 12/2008 | Jones et al. |
| 2009/0030519 A1 | 1/2009 | Falahee |
| 2009/0030520 A1 | 1/2009 | Biedermann et al. |
| 2009/0105830 A1 | 4/2009 | Jones et al. |
| 2009/0192613 A1 | 7/2009 | Wing et al. |
| 2009/0318978 A1 | 12/2009 | Podgorski et al. |
| 2010/0057206 A1 | 3/2010 | Duffield et al. |
| 2010/0217393 A1* | 8/2010 | Theofilos .................. 623/17.11 |
| 2010/0312345 A1 | 12/2010 | Duffield et al. |

\* cited by examiner

SPINAL IMPLANTS, SPINAL IMPLANT KITS, AND SURGICAL METHODS

BACKGROUND

Technical Field

The present disclosure relates to devices and methods for treating spinal conditions and, more particularly, to spinal implants configured for positioning within the intervertebral space between adjacent vertebral bodies.

Background of Related Art

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as intervertebral discs. Intervertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

SUMMARY

In accordance with the present disclosure, a spinal implant including a substantially U-shaped body, a plate, and a plurality of bone screws is provided. The substantially U-shaped body has first, second, and third walls, A first end of each of the second and third walls is joined to the first wall at opposing ends of the first wall such that the second and third walls define legs of the substantially U-shaped body. The substantially U-shaped body is configured and dimensioned to be positioned between first and second vertebral bodies. The plate has a main portion and a flange portion. The main portion of the plate defines opposed first and second surfaces and a first screw hole oriented towards the first vertebral body at an oblique angle relative to the horizontal axis of the substantially U-shaped body. The flange portion of the plate defines a second screw hole oriented towards the second vertebral body. The second screw hole is oriented substantially parallel to the horizontal axis of the substantially U-shaped body. The flange portion is coupled to the main portion such that the flange portion extends past the first surface of the main portion. Each of the bone screws is insertable through a corresponding screw hole of the plate and is attachable to bone.

In embodiments, the plate further includes one or more locking mechanisms configured such that, when a bone screw is inserted through a screw hole, the locking mechanism maintains the bone screw within the screw hole. The locking mechanism may include, for example, a locking ring positionable in the screw hole for retaining the bone screw, a lip formed in the screw hole with the screw made of a harder material than the plate such that a thread on the screw, e.g., a second screw thread disposed about the screw head, locks to the lip upon engagement of the screw with the lip, or any other suitable locking mechanism.

In embodiments, the body is configured and dimensioned such that when the body is inserted between the first and second vertebral bodies, the first surfaces of the body walls contact the first vertebral body and the second surfaces of the body walls contact the second vertebral body.

In embodiments, first and second surfaces of the body are substantially coplanar with the first and second surfaces of the main portion of the plate.

In embodiments, the plate is spaced from the body and defines a gap between the body and the plate when the body and the plate main portion are disposed between the first and second vertebral bodies.

In embodiments, the main portion of the plate includes generally uninterrupted planar surfaces and free ends of the second ends of the second and third walls of the body have generally planar surfaces that contact the generally planar surfaces of the main portion of the plate, such that the main portion of the plate and the body are repositionable relative to each other.

In embodiments, the body is formed from a first material and the plate is formed from a second material that is different from the first material. Alternatively, the body and plate may be formed from the same material.

In embodiments, the bone screw insertable through the first screw hole into the first vertebral body is configured for insertion at an oblique angle relative to the horizontal axis of the substantially U-shaped body and the bone screw insertable through the second screw hole into the second vertebral body is configured for insertion substantially parallel to the horizontal axis of the substantially U-shaped body.

Also provided in accordance with the present disclosure is a spinal interbody kit. The spinal interbody kit includes a body, a first plate, a second plate, and a plurality of bone screws. The body is configured and dimensioned to be inserted between first and second vertebral bodies. The first plate defines a plurality of screw holes and is configured to be spaced from the body to define a gap between the first plate and the body when the body and the first plate are disposed between the first and second vertebral bodies. A first screw hole of the first plate is oriented towards the first vertebral body and a second screw hole of the first plate is oriented towards the second vertebral body. The second plate may be configured similarly to and may include any or all of the features of the plate of the spinal implant described above, e.g., a main body portion and a flange portion. Each of the bone screws is insertable through a corresponding screw hole and is attachable to bone. Preferably, the bone screws are insertable through the screw holes of the first or second plate.

In embodiments, the kit further includes a plurality of locking rings. Each locking ring is positionable in one of the screw holes and is engagable with a respective bone screw for retaining the respective bone screw in the screw hole. The locking rings may be prepositioned in each hole of the first and second plates.

In embodiments, the body may further be configured similar to and may include any or all of the features of the body of the spinal implant described above.

In embodiments, the body is formed from a first material, the first plate is formed from a second material different from the first material, and the second plate is formed from a third material different from the first material. Further, the first and second plates may be formed from the same material. Alternatively, the body and the first plate and/or the second plate may be formed from the same material.

In embodiments, the material forming the body is non-metallic (e.g., polymeric materials such as polyetheretherketone), bone, or other suitable non-metallic material, while the material forming the first and second plates is metallic, e.g., titanium, or other suitable non-metallic material.

In embodiments, the body has alignment features that correspond to both the alignment features of the first plate and the alignment features of the second plate.

In embodiments, the bone screw insertable through the first screw hole of the second plate into the first vertebral body is configured for insertion at an oblique angle relative to the horizontal axis of the substantially U-shaped body and the bone screw insertable through the second screw hole of the second plate into the second vertebral body is configured for insertion substantially parallel to the horizontal axis of the substantially U-shaped body. Further, the bone screws insertable through the first and second screw holes of the first plate into the respective first and second vertebral bodies may be configured for insertion at oblique angles relative to the horizontal axis of the substantially U-shaped body.

A method of performing surgery provided in accordance with the present disclosure includes providing a surgical kit including a body, first and second plates, and a plurality of bone screws. The kit, or components thereof, may be configured similar to and may include any or all of the features of the embodiments described above. The method further includes preparing an intervertebral space between first and second vertebral bodies to receive the body, inserting the body into the prepared intervertebral space, selecting one of the first or second plates, positioning the selected plate in front of the body, inserting a first screw through the selected plate into one of the vertebral bodies, and inserting a second screw through the selected plate into the other vertebral body.

In embodiments, positioning the selected plate may further include positioning the selected plate such that a gap is defined between the body and the selected plate.

In embodiments where the body is a substantially U-shaped body, positioning the body may include positioning the body such that the open end of the substantially U-shaped body faces the direction of insertion.

In embodiments, the selected plate further includes a screw locking mechanism and inserting the screws further includes locking the screws to the plate.

In embodiments where the second plate is selected, inserting the first screw includes inserting the first screw through a screw hole of the second plate main portion and into the first vertebral body at an oblique angle relative to the horizontal axis of the body. Inserting the second screw in such embodiments may include inserting the second screw through a screw hole of the flange portion substantially parallel to the horizontal axis of the body and into the second vertebral body.

In embodiments, inserting the body includes packing the body with material prior to positioning one of the plates in front of the body.

In embodiments, inserting the body includes introducing the body and one of the first and second plates to the surgical site simultaneously under the common control of a single insertion instrument.

Another method of surgery provided in accordance with the present disclosure includes providing a surgical kit including a body, first and second plates, and a plurality of bone screws. The kit, or components thereof, may be configured similar to and may include any or all of the features of the embodiments described above. The method further includes preparing an intervertebral space between first and second vertebral bodies to receive the body, selecting one of the first or second plates, inserting the body into the prepared intervertebral space with the selected plate pre-positioned in front of the body, inserting a first screw through the selected plate into one of the vertebral bodies, and inserting a second screw through the selected plate into the other vertebral body.

In embodiments, pre-positioning the selected plate includes positioning the selected plate such that a gap is defined between the body and the selected plate.

In embodiments, inserting the body includes packing the body with material prior to pre-positioning one of the plates in front of the body.

In embodiments where the second plate is selected, inserting the first screw includes inserting the first screw through a screw hole of the second plate main portion into the first vertebral body at an oblique angle relative to the horizontal axis of the body. Further, inserting the second screw may include inserting the second screw through a screw hole of the second plate flange portion substantially parallel to the horizontal axis of the body into the second vertebral body.

BRIEF DESCRIPTION OF THE DRAWINGS

Various aspects and features of the present disclosure are described with reference to the accompanying drawing figures, wherein.

DETAILED DESCRIPTION OF THE EMBODIMENTS

Embodiments of the present disclosure are now described in detail with reference to the drawings, wherein like reference numerals identify similar or identical elements. In the drawings and in the description that follows, the term "proximal" will refer to the end of device that is closest to the operator, while the term "distal" will refer to the end of the device that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front.

Referring to FIGS. 1A-1E, one embodiment of a spinal implant assembly provided in accordance with the present disclosure is shown generally identified by reference numeral 100. Spinal implant assembly 100 generally includes a plate 110, a body 140, a plurality of bone screws 170, and a plurality of locking mechanisms 190. Plate 110 and body 140 cooperate to define a two-part spinal implant configured for positioning between adjacent vertebral bodies. Bone screws 170 are configured for securing plate 110 to the adjacent vertebral bodies, thus substantially retaining spinal implant assembly 100 in position relative to the adjacent vertebral bodies. Locking mechanisms 190 are provided to lock bone screws 170 in position within plate 110. Each of these components along with the assembly and insertion of spinal implant assembly 100 into the intervertebral space between adjacent vertebral bodies will be described in turn hereinbelow.

The various components of spinal implant assembly 100, or portions thereof, may be formed from various similar or different materials, depending on a particular purpose. For example, plate 110 and body 140 may be formed from the same or different materials. In particular, body 140 may be formed from a metallic material (similar or different to those of plate 110) or a non-metallic material, e.g., polymeric materials such as polyetheretherketone (PEEK) or organic materials such as bone, while plate 110 may be formed from a metallic material, e.g., titanium, titanium alloy, or cobalt chrome (CoCr) or a non-metallic synthetic material, e.g., polymeric materials such as PEEK, nylon absorbable polymers such as polyglycolides, polylactides, polycaprolactone, etc. Bone screw 170 may be formed from titanium, titanium alloy, CoCr or other suitable metal or polymeric material compatible with the plate. In some embodiments, bone screw 170, or at least head 174 (FIG. 4A) thereof is formed from a harder material, e.g., titanium alloy or CoCr, than the material, e.g., pure titanium, used to form plate 110, the importance of which will be described in greater detail below.

Figure 1A:
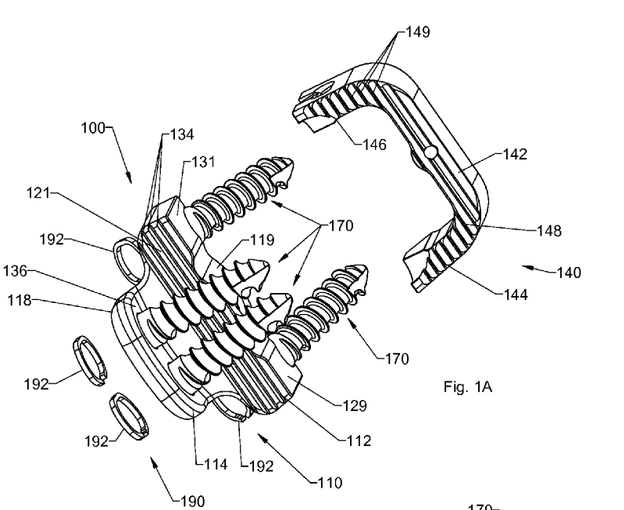
FIG. 1A is an exploded, top, perspective view of one embodiment of a spinal implant assembly provided in accordance with the present disclosure.
Figure 1B:
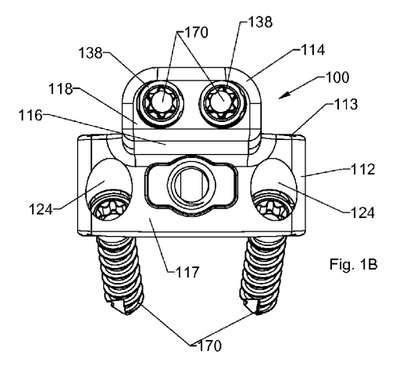
FIG. 1B is a front view of the spinal implant assembly of FIG. 1A.
Figure 1C:
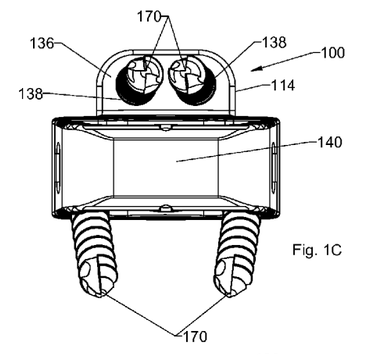
FIG. 1C is a rear view of the spinal implant assembly of FIG. 1A.
Figure 1D:
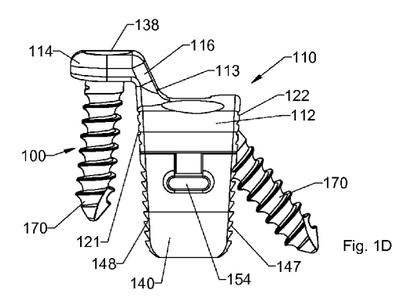
FIG. 1D is a side view of the spinal implant assembly of FIG. 1A.
Figure 1E:
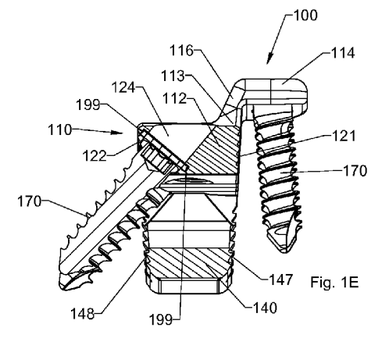
FIG. 1E is a side, cross-sectional view of the spinal implant assembly of FIG. 1A.
Figure 2A:
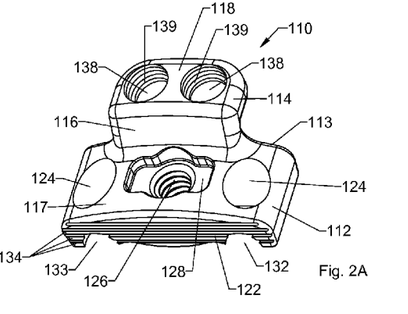
FIG. 2A is a front, perspective view of a plate of the spinal implant assembly of FIG. 1A.
Figure 2B:
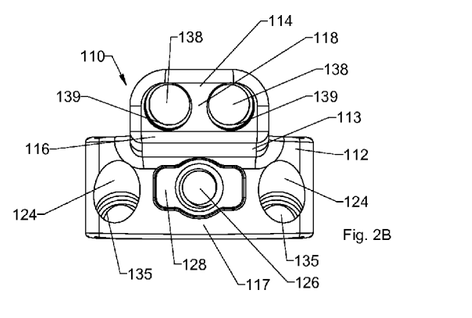
FIG. 2B is a front view of the plate of FIG. 2A.

With reference to FIGS. 2A and 2B, in conjunction with FIGS. 1A-1E, plate 110 of spinal implant assembly 100 includes a main portion 112 and a flange portion 114 extending from main portion 112. Flange portion 114 is coupled to a first edge 113 of main portion 112 via an extension portion 116 such that flange portion 114 extends vertically and outwardly from first edge 113 of main portion 112. Despite flange portion 114 being offset vertically and outwardly from main portion 112, first faces 117, 118 of main portion 112 and flange portion 114, respectively, define substantially planar surfaces disposed in substantially parallel orientation relative to one another. Main portion 112 and flange portion 114 may be monolithically formed, e.g., such that plate 110 defines a unitary or monolithic configuration, although main portion 112 and flange portion 114 may otherwise be secured to one another in any suitable fashion.

Main portion 112 of plate 110 includes a first face 117, a second, opposite face 119, a first surface 121, and a second surface 122. Main portion 112 further defines a plurality of screw holes 124 and an insertion aperture 126 extending through main portion 112 from the first face 117 to the second face 119 of main portion 112. First face 117, as mentioned above, defines a substantially planar configuration except for recess 128 defined about insertion aperture 126. Second face 119 includes first and second generally planar surfaces 129, 131 and a pair of cut-outs 132, 133 disposed between planar surfaces 129, 131 and configured to define passageways for receipt of bone screws 170. First and second surfaces 121, 122, respectively, are configured for contacting the opposed surfaces of the adjacent vertebral bodies between which spinal implant assembly 100 is positioned. First and second surfaces 121, 122 may define a plurality of ridges 134 arranged on first and second surfaces 121, 122, respectively. Ridges 134 are configured to frictionally engage the opposed surfaces of the adjacent vertebral bodies to maintain plate 110 in position relative to the adjacent vertebral bodies and to inhibit spinal implant assembly 100 from backing out of the intervertebral space.

Continuing with reference to FIGS. 2A and 2B, in conjunction with FIGS. 1A-1E, and as mentioned above, main portion 112 of plate 110 defines a plurality of screw holes 124 extending through main portion 112 from the first face 117 to the second face 119 of main portion 112. In particular, main portion 112 of plate 110 may define first and second screw holes 124 positioned towards the respective first and second sides thereof. Each screw hole 124 is obliquely angled relative to first face 117 of main portion 112 of plate 110 and a horizontal axis "X-X" of body 140, e.g., screw holes 124 extend in a non-perpendicular orientation relative to first face 117 of main portion 112 of plate 110 and the horizontal axis "X-X" of body 140. This angled configuration of screw holes 124 directs bone screws 170 inserted therethrough at similar oblique angles towards one of the vertebral bodies for engagement of bone screws 170 within the vertebral body despite main portion 112 being vertically displaced, e.g., vertically offset, relative to the vertebral body into which the bone screws 170 extending through screw holes 124 is to engage. Main portion 112 of plate 110 further defines a lip 135 disposed about and extending into each screw hole 124. Lips 135 are configured to abut heads 174 of bone screws 170 to inhibit heads 174 of bone screws 170 from passing through screw holes 124. Further, as will be described in greater detail below, a locking mechanism 190 may be positionable within or incorporated into screw holes 124 for securing heads 174 of bone screws 170 therein.

As mentioned above, main portion 112 of plate 110 defines an insertion aperture 126 extending therethrough from first face 117 to second face 119 of main portion 112. A recess 128 defined within first face 117 is disposed about insertion aperture 126. Insertion aperture 126 and recess 128 (or any other suitable portion(s) of plate 110) may be configured to receive and/or engage an insertion tool, e.g., insertion tool 400 (see FIGS. 9A-9B), to facilitate positioning of plate 110 adjacent the intervertebral space during insertion of spinal implant assembly 100 between adjacent vertebral bodies.

With continued reference to FIGS. 2A and 2B, in conjunction with FIGS. 1A-1E, flange portion 114 of plate 110 is coupled to first edge 113 of main portion 112 via an extension portion 116. Main portion 112, extension portion 116 and flange portion 114 may be integrally formed as a unitary structure. Flange portion 114 defines a first face 118 and a second, opposite face 136. Flange portion 114 further defines one or more, e.g., two, screw holes 138 extending therethrough from first face 118 to second face 136 of flange portion 114. Each screw hole 138 extends in substantially perpendicular orientation relative to first face 118 of flange portion 114 of plate 110 and in substantially parallel orientation relative to the horizontal axis "X-X" of body 140. This configuration, wherein flange portion 114 is disposed above main portion 112 of plate 110 allows flange portion 114 to be positioned adjacent, e.g., vertically aligned with, and in contact with a surface of one of the vertebral bodies. Thus, with flange portion 114 position adjacent (vertically aligned with) one of the vertebral bodies, and with screw holes 138 extending perpendicularly through flange portion 114, screw holes 138 are positioned to guide bone screws 170 into the vertebral body for securement therein in substantial parallel orientation relative to the horizontal axis "X-X" of body 140. With the plate so implanted, the flange portion abuts and is secured to the face of a vertebral body, and the main portion is offset from the flange portion by extension portion 116 and is disposed substantially between the vertebral bodies adjacent body 140 with the first and second faces of the body and main portion, respectively, substantially co-planar. Similar to screw holes 124 of main portion 112 of plate 110, screw holes 138 further define lips 139 disposed about and extending into each screw hole 138. Lips 139 are configured to abut heads 174 of bone screws 170 to inhibit heads 174 of bone screws 170 from passing through screw holes 138. Further, as will be described in greater detail below, a locking mechanism 190 may be positionable within or incorporated into screw holes 138 for securing heads 174 of bone screws 170 therein.

Figure 3:
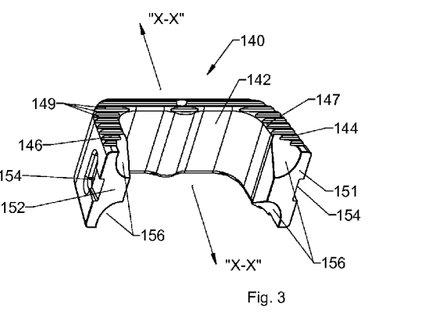
FIG. 3 is a top, perspective view of a body of the spinal implant assembly of FIG. 1A.

Referring now to FIG. 3, in conjunction with FIGS. 1A-1E, generally U-shaped body 140 of spinal implant assembly 100 is formed from a first wall 142 and second and third walls 144, 146 which extend from first wall 142 to define the legs of the generally U-shaped body 140. Body 140 defines a horizontal axis "X-X," and is configured such that walls 144, 146 extend in substantially parallel orientation relative to horizontal axis "X-X." Body 140 is positionable relative to plate 110 such that screw holes 124 of main portion 112 of plate 110 are disposed at an oblique angled relative to axis "X-X," while screw holes 138 of flange portion 114 of plate are substantially parallel to axis "X-X." Body 140 and main portion 112 of plate 110 may be dimensioned such that first and second surfaces 147, 148, respectively, of body 140 and first and second surfaces 121, 122, respectively, of main portion 112 of plate 110, are substantially coplanar with one another. Thus, upon insertion into the intervertebral space, spinal implant assembly 100 is positionable such that first surfaces 147, 121 are configured to contact a first vertebral body, while second surfaces 148, 122 are configured to contact a second vertebral body. First and second surfaces 147, 148 of body 140 may also define, similar to first and second surfaces 121, 122 of plate 110, a plurality of ridges 149 arranged in rows and configured to frictionally engage the opposed surfaces of the adjacent vertebral bodies to maintain body 140 in position relative to the adjacent vertebral bodies and to inhibit spinal implant assembly 100 from backing out of the intervertebral space.

First faces 151, 152 of second and third walls 144, 146, respectively, of body 140 are formed at the respective free ends of second and third walls 144, 146 and define generally planar configurations positioned to oppose first and second generally planar surfaces 129, 131 of second face 119 of plate 110. As a result of this configuration, plate 110 and body 140 are not constrained relative to each other and may be readily repositioned relative to one another and/or aligned with one another. Plate 110 and body 140 may be positioned in abutment with one another, e.g., wherein surfaces 151, 152 contact surfaces 129, 131, respectively, or may be spaced-apart from one another, depending on the particular procedure to be performed, anatomical considerations, etc. Body 140 further includes a pair of engagement recesses 154 defined within the outer surfaces of walls 144, 146 and configured to receive a portion of an insertion tool 400 (see FIGS. 9A-9B) for coupling body 140 to insertion tool 400 (see FIGS. 9A-9B) for insertion and placement of spinal implant assembly 100 within the intervertebral space. Plate 110 may similarly include engagement recesses (not shown), similar to recesses 238 of plate 210 (see FIG. 6A), or other suitable features (as an alternative to or in addition to insertion aperture 126) configured to engage insertion tool 400 (see FIGS. 9A-9B) for similar purposes. Body 140 of spinal implant assembly 100 further includes a plurality of cut-outs 156 configured to at least partially define passageways for receipt of bone screws 170 extending through screw holes 124, 138 and into the vertebral bodies.

Figure 4A:
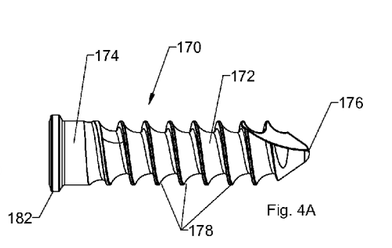
FIG. 4A is a side view of a bone screw configured for use with the spinal implant assembly of FIG. 1A.
Figure 4B:
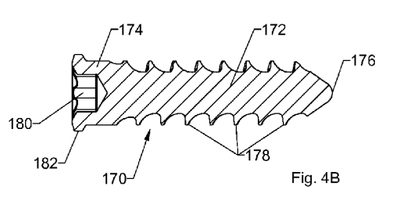
FIG. 4B is a side, cross-sectional view of the bone screw of FIG. 4A.
Figure 4C:
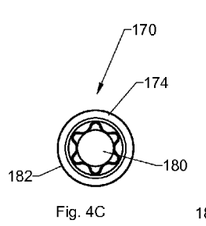
FIG. 4C is a top view of the bone screw of FIG. 4A.

Referring now to FIGS. 4A-4C, in conjunction with FIGS. 1A-1E, a bone screw 170 configured for use with spinal implant assembly 100 is shown. As can be appreciated, a plurality of bone screws 170 are configured to secure plate 110 of spinal implant assembly 100 to adjacent vertebral bodies. However, as bone screws 170 are similar to one another, only one is described in detail herein. It is also contemplated that other suitable bone screws 170 be provided for use with spinal implant assembly 100.

Bone screw 170 generally includes a shank 172 and a head 174. Shank 172 defines a distal tip 176 and pitched threading 178 disposed about shank 172. Distal tip 176 and pitched threading 178 facilitate driving bone screw 170 into bone and securement of bone screw 170 therein. Head 174 of bone screw 170 defines a tool-engaging recess 180 and an annular flange 182 defining a greater diameter than shank 172. Tool-engaging recess 180 defines a configuration, e.g., a 6-point star or other suitable configuration, shaped complementary to a driving end of an insertion tool (not shown) to facilitate engagement of the insertion tool (not shown) with head 174 of bone screw 170 for rotational driving of bone screw 170 into a vertebral body. Flanges 182 of heads 174 of bone screws 170 are configured to be seated within lips 135, 139 of screw holes 124, 138, respectively, to inhibit bone screws 170 from passing through screw holes 124, 138. As mentioned above, in some embodiments, bone screws 170 (or heads 174 thereof) formed from a harder material than plate 110 with threads (not shown) are provided on heads 174 to engage and deform lips 135, 139 in screw holes 124, 138 to lock bone screws 170 within plate 110. See, for example, U.S. Pat. No. 6,322,562 to Wolter, the entire contents of which are hereby incorporated by reference herein. Alternatively, other suitable locking mechanisms 190, e.g., locking rings 192, may be provided.

Figure 5:
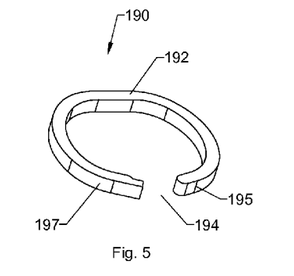
FIG. 5 is a top, perspective view of a locking ring configured for use with the spinal implant assembly of FIG. 1A.

Turning now to FIG. 5, in conjunction with FIGS. 1A-1E, as mentioned above, locking mechanism 190 may include a locking ring 192 configured for engagement within one or more of screw holes 124, 138 to retain screw head 174 between locking ring 192 and the lip 135, 139 of the screw hole 124, 138, respectively. Locking ring 192 defines a generally annular configuration having a disconnect, or interruption 194. Thus, with interruption 194 formed in locking ring 192, locking ring 192 defines first and second resilient legs 195, 197. In an at-rest condition, locking ring 192 defines a diameter that approximates or is larger than a diameter of screw holes 124, 138. In a compressed condition, legs 195, 197 are urged inwardly to define a diameter of locking ring 192 that is smaller than the diameter of screw holes 124, 138, thus permitting locking ring 192 to be inserted into the screw hole 124, 138 after insertion of bone screw 170 therethrough to retain head 174 of bone screw 170 between lip 135, 139 and locking ring 192. The resilient bias of locking ring 192 towards the at-rest condition retains locking ring 192 in position, thus inhibiting bone screw 170 from backing out of the screw hole 124, 138. Further, an annular slot 199 (see FIG. 1E) may be formed within each screw hole 124, 138. Slot 199 is configured to receive locking ring 192 upon return of locking ring 192 under bias towards the at-rest position, thus securing locking ring 192 within the screw holes 124, 138. In some embodiments, plate 110 may be pre-loaded with locking rings 192. In such embodiments, upon insertion of bone screws 170 into screw holes 124, 138, heads 174 of bone screws 170 urge locking ring 192 to expand beyond the at-rest position, thus permitting passage of heads 174 through locking rings 192. Upon return of locking rings 192 towards the at-rest position, locking rings 192 retains heads 174 within screw holes 124, 138, similarly as described above. Plate 110 need not be pre-loaded with locking rings 192. Further, other suitable locking mechanisms (not shown) for securing bone screws 170 within plate 110 are also contemplated.

Figure 6A:
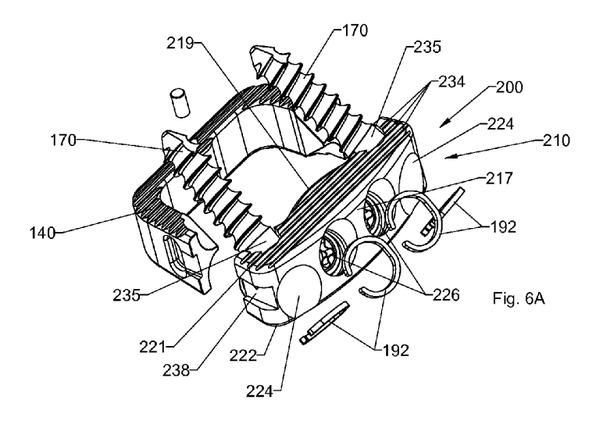
FIG. 6A is an exploded, top, perspective view of another embodiment of a spinal implant assembly provided in accordance with the present disclosure.
Figure 6B:
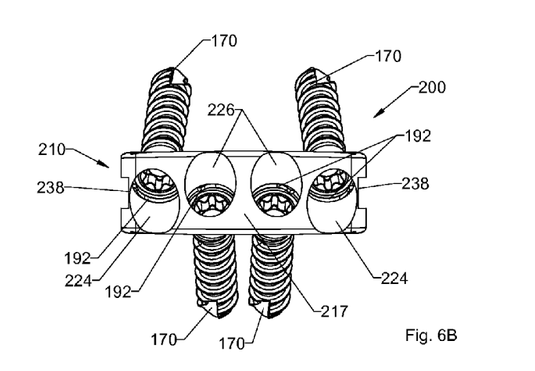
FIG. 6B is a front view of the spinal implant assembly of FIG. 6A.
Figure 6C:
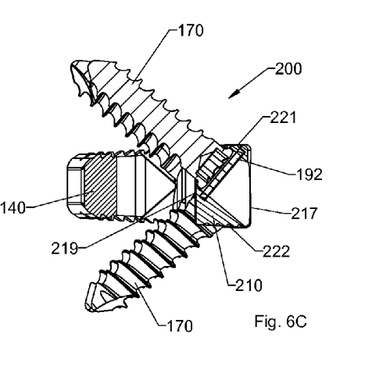
FIG. 6C is a side, cross-sectional view of the spinal implant assembly of FIG. 6A.
Figure 7:
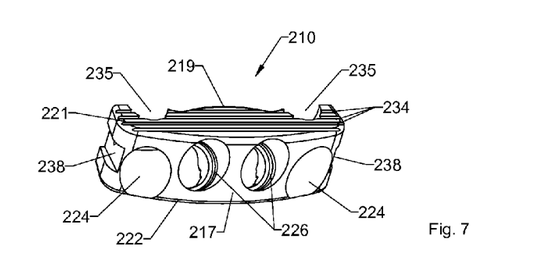
FIG. 7 is a front, perspective view of a plate of the spinal implant assembly of FIG. 6A.

Turning now to FIGS. 6A-7, another embodiment of a spinal implant assembly provided in accordance with the present disclosure is shown generally identified by reference numeral 200. Spinal implant assembly 200 differs from spinal implant assembly 100 (FIGS. 1A-1E) in the configuration of plate 210 as compared to plate 110 (FIGS. 1A-1E). That is, depending on the particular procedure to be performed, anatomical considerations, etc., body 140 may be used in conjunction with plate 110 (FIGS. 1A-1E) or plate 210, thus forming the desired spinal implant assembly 100, 200 (FIGS. 1A-1E and 6A-6C, respectively). Bone screws 170 and locking rings 190 are likewise configured for use with either of the spinal implant assemblies 100, 200 (FIGS. 1A-1E and 6A-6C, respectively). Accordingly, only plate 210 of spinal implant assembly 200 will be described below, as the other components of spinal implant assembly 200 are similar to those of spinal implant assembly 100 (FIGS. 1A-1E), described above. Further, plate 210 may include any or all of the features of plate 110 (FIGS. 1A-1E), described above, to the extent they are consistent or not expressly contradicted below.

Plate 210 of spinal implant assembly 200 defines a generally rectangular-shaped configuration having a first face 217, a second, opposite face 219, a first surface 221, and a second surface 222. A plurality of screw holes 224, 226 extend through plate 210 from the first face 217 to the second face 219 thereof. Screw holes 224 are angled in a first direction relative to first face 217 of plate 210, e.g., screw holes 224 extend in a non-perpendicular orientation relative to first face 217 such that screw holes 224 direct bone screws 170 inserted therethrough towards one of the vertebral bodies for engagement of bone screws 170 within the vertebral body, despite the fact that plate 210 is vertically offset, e.g., vertically displaced, relative to the vertebral body. Screw holes 226, on the other hand, are angled in a second, different direction relative to first face 217 of plate 210 such that screw holes 226 direct bone screws 170 inserted therethrough towards the other vertebral body for engagement of bone screws 170 therein, despite the fact that plate 210 is vertically offset, e.g., vertically displaced, relative to the vertebral body. Screw holes 224 are shown disposed towards the outer portion of plate 210, while screw holes 226 are disposed towards a middle portion of plate 210. However, any other suitable arrangement of screw holes 224, 226 is also contemplated. Screws holes 224, 226 may otherwise be configured similar to screw holes 124, 138 (FIGS. 1A-1E), described above.

First and second surfaces 221, 222, respectively, of plate 210 are configured for contacting the opposed surfaces of the adjacent vertebral bodies between which spinal implant assembly 200 is positioned. First and second surfaces 221, 222 may define a plurality of ridges 234 arranged in rows on first and second surfaces 221, 222, respectively, that are configured to frictionally engage the opposed surfaces of the adjacent vertebral bodies to maintain plate 210 in position relative to the adjacent vertebral bodies and to inhibit spinal implant assembly 200 from backing out of the intervertebral space. Plate 210 is configured and dimensioned such that first and second surfaces 221, 222 of plate 210 and first and second surfaces 147, 148, respectively, of body 140 are substantially coplanar with one another. Thus, upon insertion into the intervertebral space, spinal implant assembly 200 is positionable such that first surfaces 147, 221 are configured to contact a first vertebral body, while second surfaces 148, 222 are configured to contact a second vertebral body. Further, body 140 and plate 210 are positionable relative to one another such that screw holes 224, 226 of plate 210 are disposed at an oblique angled relative to axis "X-X" of body 140.

Second face 219 of plate 210 may define a plurality of cut-outs 235 configured to at least partially define passageways for receipt of bone screws 170. Further, at least a portion of second face 219 may define a generally planar configuration positioned to oppose surfaces 151, 152 of body 140 to permit repositioning and/or alignment of plate 210 relative to body. Plate 210 also includes a pair of engagement recesses 238 configured to receive a portion of an insertion tool 400 (see FIGS. 9A-9B) for insertion and placement of spinal implant assembly 200 within the intervertebral space, e.g., in conjunction with engagement recesses 154 defined within the outer surfaces of walls 144, 146 of body 140, as will be described in greater detail below.

Figure 8A:
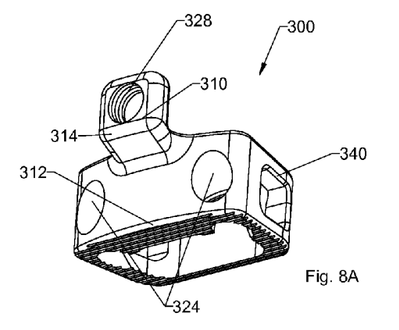
FIG. 8A is a bottom, perspective view of a unitary spinal implant provided in accordance with the present disclosure.
Figure 8B:
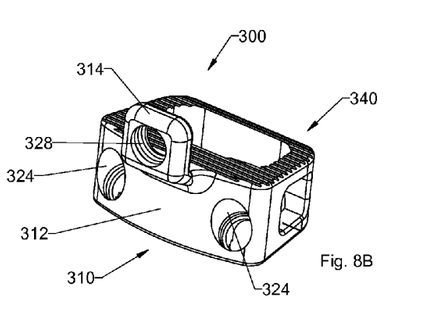
FIG. 8B is a top, perspective view of the unitary spinal implant of FIG. 8A.
Figure 8C:
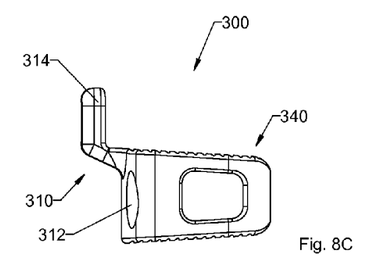
FIG. 8C is a side view of the unitary spinal implant of FIG. 8A.

Referring to FIGS. 8A-8C, another embodiment of a spinal implant assembly is shown generally designated by reference numeral 300. Spinal implant assembly 300 is a unitary implant, e.g., wherein plate 310 and body 340 are formed as a single component. Body 340 defines a generally U-shaped configuration, while plate 310 includes a main portion 312 and a flange portion 314. Main portion 312 defines a pair of angled screw holes 324 therethrough, while flange portion 314 defines a generally perpendicular screw hole 328 extending therethrough, similarly as described above with respect to plate 110 (FIGS. 1A-1E). Spinal implant assembly 300 may otherwise be similar to and/or include any or all of the features of spinal implant assemblies 100, 200 described above.

Figure 9A:
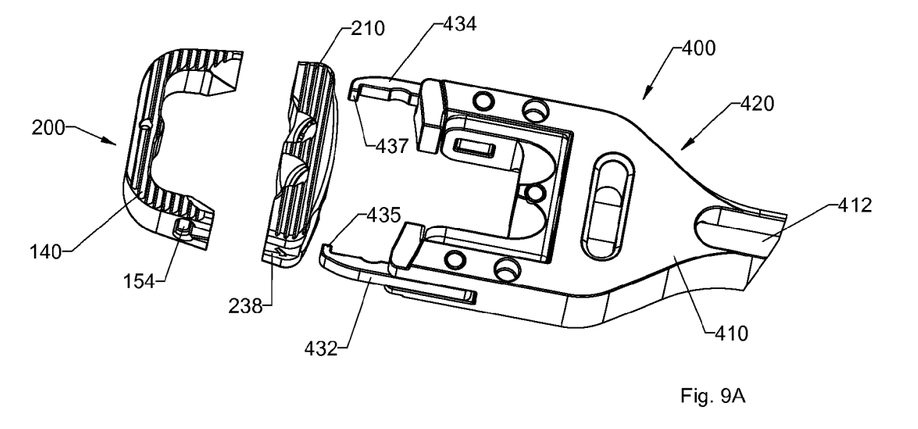
FIG. 9A is an exploded, top, perspective view of an insertion instrument shown in use with the spinal implant assembly of FIG. 6A.
Figure 9B:
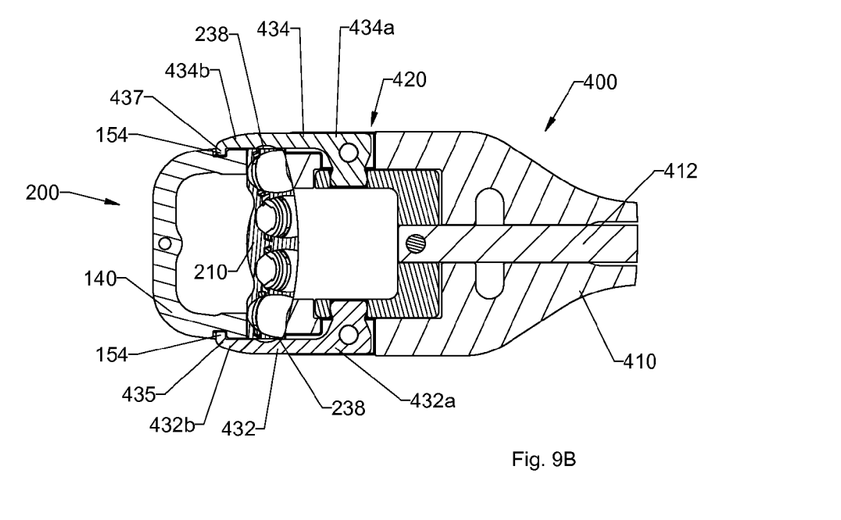
FIG. 9B is an enlarged, cross-sectional view of the insertion instrument of FIG. 9A engaged with the spinal implant assembly of FIG. 6A.

Referring to FIGS. 9A-9B, an insertion instrument 400 configured for use with either or both of spinal implant assemblies 100, 200 is shown. That is, despite being shown in use with spinal implant assembly 200, insertion instrument 400 may similarly be used for insertion of spinal implant assembly 100. Insertion instrument 400 includes an elongated body 410 having an end effector assembly 420 disposed at the distal end of elongated body 410. End effector assembly 420 includes a pair of spaced-apart arms 432, 434, at least one of which is movable relative to the other. More specifically, an actuating bar 412 slidably disposed within elongated body 410 may be coupled to first arm 432 at the distal end of actuating bar 412 such that translation of actuating bar 412 relative to first arm 432 effects pivoting of first arm 432 relative to second arm 434 between a substantially parallel orientation, for retaining implant assembly 200 therebetween, and an obliquely-angled orientation, for permitting insertion and withdrawal of implant assembly 200 from between arms 432, 434 of end effector assembly 430.

Each arm 432, 434 of end effector assembly 430 includes a fixed end 432a, 434a and a free end 432b, 434b. Plate 210 of spinal implant assembly 200 is configured for positioning between arms 432, 434 adjacent fixed ends 432a, 434a, respectively, of arms 432, 434. Further, plate 210 may be retained between arms 432, 434 via engagement of arms 432, 434 within recesses 238 of plate 210. Body 140 is configured for positioning between arms 432, 434 adjacent free ends 432b, 434b, respectively, of arms 432, 434. Arms 432, 434 each include an inwardly-facing protrusion 435, 437, respectively, disposed towards the free end 432b, 434b thereof that is configured for engagement within one of the engagement recesses 154 of body 140 to retain body 140 between arms 432, 434. Thus, the above-described configuration allows both plate 210 and body 140 to be inserted into the intervertebral space in cooperation with one another and under control of insertion instrument 400.

With reference to FIGS. 1A-7, the insertion of a spinal implant assembly 100, 200 into the intervertebral space between adjacent vertebral bodies during the course of a spinal surgical procedure is described. Initially, the intervertebral space is prepared, e.g., damaged or diseased tissue is removed. Next, body 140, lead by first wall 142, is inserted into the intervertebral space between the adjacent vertebral bodies. At this point, or prior thereto, if the particular procedure so dictates, the interior space defined by the generally U-shaped body 140 may be packed with bone in-growth material, drugs, or other suitable materials or compounds. In some embodiments, body 140 may be inserted into the intervertebral space with the opening of the generally U-shaped body 140 facing the direction of insertion, e.g., opposite the configuration noted above. In such embodiments, the body and plate may be sequentially inserted, or the insertion instrument, e.g., insertion instrument 400 (FIGS. 9A-9B), would engage body 140 about the outer surface thereof adjacent first wall 142 to facilitate insertion of body 140 lead by legs 144, 146. It is envisioned that insertion instrument 400 (FIGS. 9A-9B be further configured such that inwardly-facing protrusions 435, 437 of arms 432, 434, respectively, may be engaged within engagement recesses 154 of body 140 to retain body 140 between arms 432, 434 in this orientation.

As mentioned above, body 140 may alternatively be inserted into the intervertebral space in cooperation with the selected plate 110, 210, under common control of insertion instrument 400 (FIGS. 9A-9B). In such embodiments, the interior space of body 140 may be packed with bone in-growth material, drugs, or other suitable materials or compounds upon or prior to engagement of body 140 and the selected plate 110, 210 with insertion instrument 400 (FIGS. 9A-9B).

With body 140 positioned within the intervertebral space, an appropriate plate 110, 210 is selected. As mentioned above, the plate 110, 210 selected may depend on the particular procedure to be performed, anatomical considerations, and/or other factors. For example, plate 210 maybe used for applications where surgical access permits screws to be driven at opposing oblique angles. Plate 110, on the other hand, may be particularly useful in instances where anatomy makes it difficult to drive screws at opposed oblique angles, e.g., at L5:S1 or C1:C2. If plate 110 is selected, for example, plate 110 is positioned adjacent but externally of the intervertebral space such that main portion 112 of plate 110 is positioned adjacent body 140, e.g., vertically between the vertebral bodies, and such that flange portion 114 is positioned adjacent one of the vertebral bodies. Plate 110 may then be more finely positioned relative to body 140 to define a gap between plate 110 and second and third walls 144, 146 of body 140, or may be disposed in abutment therewith. The insertion and/or positioning of plate 110 may be achieved using an insertion tool, e.g., insertion tool 400 (FIGS. 9A-9B). Alternatively, body 140 and plate 110 may be inserted in cooperation with one another, e.g., wherein both body 140 and plate 110 are engaged to and under the control of insertion tool 400 (FIGS. 9A-9B), similarly as described above. Plate 210 may be positioned and/or inserted similar to plate 110, in embodiments where plate 210 is selected.

Once plate 110 is moved into proper position, first and second bone screws 170 are inserted through the respective first and second screw holes 124 of main portion 112 of plate 110 and are driven into one of the adjacent vertebral bodies. More specifically, due to the obliquely angled configuration of screw holes 124 relative to axis "X-X," as mentioned above, bone screws 170 are guided through screw holes 124 and into the vertebral body. Next, third and fourth bone screws 170 are inserted through the respective first and second screw holes 138 of flange portion 114 of plate 110 and are driven into the other adjacent vertebral body. The parallel orientation of screw holes 138 guide bone screws 170 therethrough and into the adjacent vertebral body. Once bone screws 170 are positioned as desired, locking rings 192 may be inserted into screw holes 124, 138 to lock the heads 174 of bone screws 170 therein, thus retaining plate 112 in position. Plate 110, in turn, blocks the exit to the intervertebral space, thus inhibiting body 140 from backing out of the intervertebral space, while still permitting repositioning of body 140 relative to plate 110.

Figure 10:
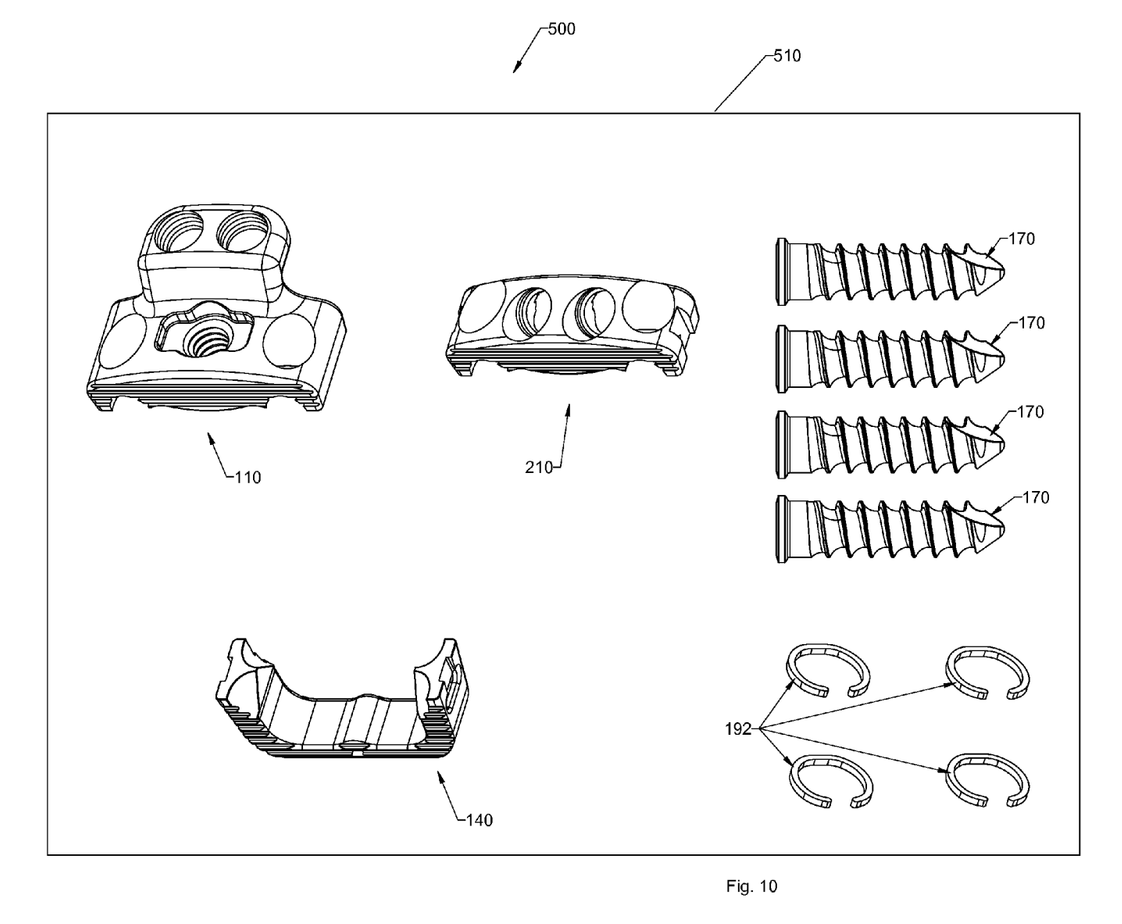
FIG. 10 illustrates a surgical kit provided in accordance with the present disclosure.

Referring now to FIG. 10, also provided in accordance with the present disclosure is a surgical kit 500 containing various components to facilitate surgery with interchangeable parts, as the procedure, anatomy, and/or other factors may dictate. Surgical kit 500 includes an enclosure or housing 510 that retains a plurality of bone screws 170 (of similar or different type), a plurality of locking rings 192 (and/or other suitable locking mechanisms), one or more bodies 140 (of similar or different type), one or more plates 110, and one or more plates 210. Different sizes of bodies 140, screws 170, plates 110, plates 210 or plates 300 may be included. Surgical kit 500 provides the surgeon with flexibility in selecting the components best suited to obtain optimal surgical results. That is, using the example detailed above, providing one or more plates 110 and one or more plates 210 in a single kit 500 allows the surgeon to readily select the appropriate plate 110, 210 from the same kit 500. The other components of kit 500, e.g., bone screws 170, body 140, and/or locking rings 192, may be configured for use with both plates 110 and 120, although these or additional components unique to plates 110 and/or 120 may also be provided. Kit 500 may further includes one or more instruments, e.g., insertion instrument 400 (FIGS. 9A-9B), for use in preparation of the surgical site and/or insertion of body 140, plates 110, 210, or bone screws 170.

In use, kit 500 is delivered to the operating room in sterile condition. The surgeon accesses and prepares the surgical site, possibly using instruments included in the kit. The surgeon selects the size of body to be used, such as by using trial implants included in the kit (not shown), to select the size of body 140 and plate 110 or 210 to be used with the body. The body is prepared for insertion, such as by packing the open center with bone or bone substitute or bone growth material, and is inserted into the prepared space between the vertebral bodies. The selected plate 110 or 210 is then placed adjacent the body and screws 170 are driven through the holes in the plate to anchor the plate to the vertebral bodies. Alternatively, the body and plate may be mounted to insertion instrument 400 and inserted into the surgical site simultaneously. As a further alternative, if included in the kit the surgeon may select unitary implant 300 and insert that implant into the patient. Advantageously, by including a variety of bodies 140 and plates 110, 210, and possibly 300, in kit 500, the surgeon can select the unitary or multipart implant that fits the pathology of the patient identified during surgery by the surgeon. Factors that may be considered by the surgeon in selecting the implant configuration may include whether surgical access facilitates insertion of screws at opposed oblique angles, as required for plates 210. If access to deliver screws at opposed oblique angles is restricted, the surgeon may select implant 110. As discussed above, it is contemplated that plates 110, 210 may be interchangeable with a common body 140 or set of bodies 140 of different sizes. It is also contemplates that bodies specifically designed for each plate and not interchangeable between plates 110, 210 may be provided. Kit 500 may be shipped to the surgical center or hospital pre-sterilized and sealed in a sterile container or wrapping, or may be presented to the surgical center or hospital non-sterile to be sterilized at the surgical center or hospital, such as in an autoclave.

It will be understood that various modifications may be made to the embodiments of the present disclosure. By way of example, the body and plate preferably are independent of one another in order to permit the surgeon flexibility in positioning each structure for optimal surgical results. However, it is contemplated that the plate and body may be coupled together, such as by a vertical or horizontal dovetail joint, in order to maintain the body and plate in a predetermined orientation. Therefore, the above description should not be construed as limiting, but merely as exemplifications of embodiments. Those skilled in the art will envision other modifications within the scope and spirit of the present disclosure.

What is claimed is:

1. A spinal implant comprising:
    a substantially U-shaped body defining an upper body surface, a lower body surface, an inner body surface, and an outer body surface, the substantially U-shaped body having a first wall, a second wall, and a third wall, a first end of each of the second wall and the third wall joined to the first wall at opposing ends of the first wall such that the second wall and the third wall define legs of the substantially U-shaped body, a second, free end of each of the second wall and the third wall defining a face, each face defining an uninterrupted planar wall surface bounded by and occupying an entire area defined between the upper body surface, the lower body surface, the inner body surface, and the outer body surface, the substantially U-shaped body configured and dimensioned to be positioned between a first vertebral body and a second vertebral body;
    a plate having a main portion and a flange portion, the main portion having:
        a first face oriented away from the substantially U-shaped body,
        a second face oriented towards the substantially U-shaped body, the second face defining a first uninterrupted planar plate surface and a second uninterrupted planar plate surface, the first uninterrupted planar plate surface and the second uninterrupted planar plate surface configured for positioning adjacent to and in opposed relation relative to the first uninterrupted planar wall surface and the second uninterrupted planar wall surface, respectively, so as to enable slidable repositioning of the plate and the substantially U-shaped body relative to each other along a plane parallel to the uninterrupted planar wall surfaces and the uninterrupted planar plate surfaces,
        an upper plate surface and a lower plate surface, and
        a first screw hole oriented towards the first vertebral body at an oblique angle relative to a horizontal axis of the substantially U-shaped body,
    the flange portion having a second screw hole oriented towards the second vertebral body with the second screw hole oriented substantially parallel to the horizontal axis of the substantially U-shaped body, the flange portion coupled to the main portion such that the flange portion extends past the upper plate surface of the main portion; and
    a plurality of bone screws, each bone screw of the plurality of bone screws insertable through a corresponding screw hole of a plurality of screw holes of the plate and capable of attaching to bone.

2. The spinal implant of claim 1, wherein the plate further comprises at least one locking mechanism, such that when a bone screw of the plurality of bone screws is inserted through a screw hole of the plurality of screw holes, the locking mechanism maintains the bone screw within the screw hole.

3. The spinal implant of claim 2, wherein the locking mechanism comprises a locking ring positionable in the screw hole for retaining the bone screw.

4. The spinal implant of claim 3, wherein the locking mechanism comprises a locking ring positioned in each screw hole of the plurality of screw holes to retain the plurality of bone screws.

5. The spinal implant of claim 2, wherein the locking mechanism comprises a lip formed in each screw hole of the plurality of screw holes, with the plate made of a first material and the plurality of bone screws made of a second, harder material such that each bone screw of the plurality of bone screws locks to the lip upon engagement of the bone screw of the plurality of bone screws with the lip.

6. The spinal implant of claim 1, wherein the substantially U-shaped body is configured and dimensioned so that when the substantially U-shaped body is inserted between the first vertebral body and the second vertebral body, the upper body surface contacts the first vertebral body and the lower body surface contacts the second vertebral body.

7. The spinal implant of claim 1, wherein the upper body surface and the lower body surface are substantially coplanar with the upper plate surface and the lower plate surface, respectively.

8. The spinal implant of claim 1, wherein the first uninterrupted planar plate surface and the second uninterrupted planar plate surface are spaced from the uninterrupted planar wall surfaces of the faces of the second wall and the third wall, respectively, of the substantially U-shaped body to define a gap therebetween when the substantially U-shaped body and the plate main portion are disposed between the first vertebral body and the second vertebral body.

9. The spinal implant of claim 1, wherein the first uninterrupted planar surface and the second uninterrupted planar surface of the main portion of the plate and the uninterrupted planar wall surfaces of the faces of the second wall and the third wall, respectively, of the substantially U-shaped body are disposed in slidable contact with each other when the substantially U-shaped body and the plate main portion are disposed between the first vertebral body and the second vertebral body.

10. The spinal implant of claim 1, wherein the substantially U-shaped body is formed from a first material and the plate is formed from a second material different from the first material.

11. The spinal implant of claim 1, wherein the bone screw of the plurality of bone screws that is insertable through a first screw hole of the plurality of screw holes into the first vertebral body is configured for insertion at an oblique angle relative to the horizontal axis of the substantially U-shaped body, and wherein the bone screw of the plurality of bone screws that is insertable through a second screw hole of the plurality of screw holes into the second vertebral body is configured for insertion substantially parallel to the horizontal axis of the substantially U-shaped body.

12. The spinal implant of claim 1, wherein the plate and the substantially U-shaped body are slidably repositionable relative to each other along a plane parallel to both the uninterrupted planar wall surfaces and the uninterrupted planar plate surfaces in a direction transverse to the horizontal axis of the substantially U-shaped body.

13. The spinal implant of claim 12, wherein the plate and the substantially U-shaped body are slidably repositionable relative to each other along a plane parallel to both the uninterrupted planar wall surfaces and the uninterrupted planar plate surfaces in a direction perpendicular to the horizontal axis of the substantially U-shaped body.

14. A spinal implant comprising:
a substantially U-shaped body defining an upper body surface, a lower body surface an inner body surface, and an outer body surface, the substantially U-shaped body and configured and dimensioned so that when the substantially U-shaped body is inserted between a first vertebral body and a second vertebral body, the upper body surface contacts the first vertebral body and the lower body surface contacts the second vertebral body, the substantially U-shaped body defining a first leg and a second leg each having a free end, the free end of the first leg defining a first uninterrupted planar leg surface bounded by and occupying an entire first area defined between the upper body surface, the lower body surface, the inner body surface, and the outer body surface, the free end of the second leg defining a second uninterrupted planar leg surface bounded by and occupying an entire second area defined between the upper body surface, the lower body surface, the inner body surface, and the outer body surface; and a plate including:
a main portion including:
an upper main portion surface and a lower main portion surface;
a first face oriented away from the substantially U-shaped body;
a second face oriented towards the substantially U-shaped body, the second face defining a first uninterrupted planar plate surface and a second uninterrupted planar plate surface, the first uninterrupted planar plate surface and the second uninterrupted planar plate surface configured for positioning adjacent to and in opposed relation relative to the first uninterrupted planar leg surface and the second uninterrupted planar leg surface, respectively, so as to enable slidable repositioning of the plate and the substantially U-shaped body relative to each other along a plane parallel to both the uninterrupted planar leg surfaces and the uninterrupted planar plate surfaces; and
a first screw hole configured to receive a first bone screw; and
a flange portion having a second screw hole configured to receive a second bone screw, the flange portion coupled to the main portion such that the flange portion extends past the upper main portion surface of the main portion.

15. The spinal implant of claim 14, wherein the upper body surface and the lower body surface are substantially coplanar with the upper main portion surface and the lower main portion surface, respectively.

16. The spinal implant of claim 14, wherein the first uninterrupted planar plate surface and the second uninterrupted planar plate surface are spaced from the first uninterrupted planar leg surface and the second uninterrupted planar leg surface, respectively, to define gaps therebetween when the substantially U-shaped body and the plate main portion are disposed between the first vertebral body and the second vertebral body.

17. The spinal implant of claim 14, wherein the first uninterrupted planar plate surface and the second uninterrupted planar plate surface are disposed in slidable contact with the first uninterrupted planar leg surface and the second uninterrupted planar leg surface, respectively, when the substantially U-shaped body and the plate main portion are disposed between the first vertebral body and the second vertebral body.

18. The spinal implant of claim 14, wherein the plate and the substantially U-shaped body are slidably repositionable relative to each other along a plane parallel to both the uninterrupted planar leg surfaces and the uninterrupted planar plate surfaces in a direction transverse to the horizontal axis of the substantially U-shaped body.

19. The spinal implant of claim 18, wherein the plate and the substantially U-shaped body are slidably repositionable relative to each other along a plane parallel to both the uninterrupted planar leg surfaces and the uninterrupted planar plate surfaces in a direction perpendicular to the horizontal axis of the substantially U-shaped body.

\* \* \* \* \*